United States Patent
Coy et al.

(10) Patent No.: US 6,703,481 B1
(45) Date of Patent: *Mar. 9, 2004

(54) SOMATOSTATIN ANTAGONISTS

(75) Inventors: David H. Coy, New Orleans, LA (US); Barry Morgan, Franklin, MA (US); William Murphy, Slidell, LA (US)

(73) Assignees: The Administration of the Tulane Educational Fund, New Orleans, LA (US); Societe de Conseils de Recherches et d'Applications Scientifiques, S.A.S., Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 09/670,249

(22) Filed: Sep. 26, 2000

Related U.S. Application Data

(63) Continuation of application No. 08/855,204, filed on May 13, 1997, now Pat. No. 6,262,229.
(60) Provisional application No. 60/032,358, filed on Dec. 4, 1996.

(51) Int. Cl.[7] .................... A61K 38/31; C07K 7/00
(52) U.S. Cl. ................. 530/311; 530/317; 530/328; 530/329; 514/11; 514/16
(58) Field of Search ................. 530/311, 317, 530/328, 329; 514/11, 16

(56) References Cited

U.S. PATENT DOCUMENTS

| | | | |
|---|---|---|---|
| 4,395,403 A | 7/1983 | Bauer et al. | 424/177 |
| 4,435,385 A | 3/1984 | Bauer et al. | 424/177 |
| 4,650,787 A | 3/1987 | Schally et al. | 514/11 |
| 4,728,638 A | 3/1988 | Bauer et al. | 514/11 |
| 4,853,371 A | 8/1989 | Coy et al. | 514/12 |
| 4,904,642 A | 2/1990 | Coy et al. | 514/11 |
| 5,462,926 A | 10/1995 | Coy et al. | 514/16 |
| 5,506,339 A | 4/1996 | Coy et al. | 530/311 |
| 5,597,894 A | 1/1997 | Coy et al. | 530/311 |
| 5,633,263 A | 5/1997 | Coy et al. | 530/311 |
| 5,846,934 A | 12/1998 | Bass et al. | 514/11 |
| 5,965,744 A | 10/1999 | Weichert et al. | 548/338.1 |
| 6,262,229 B1 * | 7/2001 | Coy et al. | 530/311 |

FOREIGN PATENT DOCUMENTS

| | | |
|---|---|---|
| EP | 0 029 579 | 11/1980 |
| EP | 0 203 031 | 4/1985 |
| EP | 0 187 622 | 12/1985 |
| EP | 0 389 180 B1 | 3/1990 |
| EP | 0 395 417 A1 | 10/1990 |
| EP | 0 791 603 | 8/1997 |
| HU | 217635 | 3/2000 |
| WO | WO 88/05052 | 7/1988 |
| WO | WO 89/04666 | 6/1989 |
| WO | WO 90/12811 | 11/1990 |
| WO | WO 97/11962 | 4/1997 |

OTHER PUBLICATIONS

Hoyer et al., "Molecular Pharmacology of Somatostatin Receptors", Naunn–Schmiedeberg's Arch. Pharmacol. (1994) 350:441–453.

Raynor et al., "Cloned Somatostatin Receptors: Identification of Subtype–Selective Peptides and Demonstration of High Affinity Binding of Linear Peptides", Molecular Pharmacology, 43:838–844, (1993).

Lamberts et al., "The Role of Somatostatin and Its Analogs in the Diagnosis and Treatment of Tumors",. Endocrine Reviews, vol. 12, No. 4, pp. 450–482, (1991).

Reisine, et al., "Molecular Biology of Somatostatin Receptors", Endocrine Reviews, vol. 16., No. 4, pp. 427–442, (1995).

Patel et al., "The Somatostatin Receptor Family", Life Sciences, Vol 57, No. 13, pp. 1249–1265, (1995).

Hofland, et al., "Somatostatin Analogs Clinical Application in Relation to Human Somatostatin Receptor Subtypes", Biomedical Pharmacology, vol. 50, No. 3, pp. 287–297 (1995).

Reisine, et al., "Molecular Properties of Somatostatin Receptors", Neuroscience, vol. 67, No. 4, pp. 777–790, (1995).

Bass, et al., "Identification and Characterization of Novel Somatostatin Antagonists", Molecular Pharmacology, 50:709–715 (1996).

Patel et al., "Subtype Selectivity of Peptide Analogs for All Five Cloned Human Somatostatin Receptors", Endocrinology, vol. 135, No. 6, pp. 2814–2817, (1994).

Heiman et al., Neuroendocrinology, 45:429–436 (1987).

Lloyd, et al., Am. J. Physiol., 268:G102–G106 (1995).

Rossowski, W.I., Coy, D.H., Biochemcial and Biophysical Research Comm., 197:366–371 (1993).

Bass et al., Molecular Pharmacology, 50:709–715 (1996).

Osapay, George et al: "Lanthionine–Somatostatin Analogs: Synthesis, Characterization, Biological Activity, and Enzymatic Stability Studies", J. Med. Chem. (1997), 40(14), 2241–2251 CODEN: JMCMAR; ISSN: 0022–2623, XP002071716.

Melacini, Giuseppe et al: "A Refined Model for the Somatostatin Pharmacophore: Conformational Analysis of Lanthionine–Sandostatin Analogs", J. Med. Chem. (1997), 40(14), 2252–2258 CODEN: JMCMAR: ISSN: 0022–2623, XP002071717.

* cited by examiner

*Primary Examiner*—Dwayne C. Jones
*Assistant Examiner*—C. Delacroix-Muirheid
(74) *Attorney, Agent, or Firm*—Fish & Richardson; Brian R. Morrill; Alan F. Feeney

(57) ABSTRACT

The invention features somatostatin antagonists having a D-amino acid at the second residue.

5 Claims, No Drawings

SOMATOSTATIN ANTAGONISTS

CROSS REFERENCE TO RELATED APPLICATIONS

This is a continuation of application Ser. No. 08/855,204, filed May 13, 1997, [now abandoned] now U.S. Pat. No. 6,262,229 a non-provisional application that claims the benefit of U.S. application Ser. No. 60/032,358, filed Dec. 4, 1996, each of which is hereby incorporated herein by reference in its entirety.

BACKGROUND OF THE INVENTION

Native somatostatin is comprised of both a 14-amino acid isoform (somatostatin-14) and a 28-amino acid isoform (somatostatin-28). Heiman, et al., Neuroendocrinology, 45:429–436 (1987). Because of the short half-life of the native somatostatin, various somatostatin analogs have been developed, e.g., for the treatment of acromegaly. Raynor, et al., Molecular Pharmacol. 43:838 (1993). Five distinct somatostatin receptors have been identified and characterized. Hoyer, et al., Naunyn-Schmiedeberg's Arch. Pharmacol., 350:441 (1994). Somatostatin produces a variety of effects, including modulation of hormone release, e.g., growth hormone, glucagon, insulin, amylin, and neurotransmitter release. Some of these effects have been associated with its binding to a specific somatostatin receptor. For example, the inhibition of growth hormone has been attributed to the somatostatin type-2 receptor ("SSTR-2") (Raynor, et al., Molecular Pharmacol. 43:838 (1993); Lloyd, et al., Am. J. Physiol. 268:G102 (1995)) while the inhibition of insulin has been attributed to the somatostatin type-5 receptor ("SSTR-5") (Coy, et al. 197:366–371 (1993)). The following invention relates to a novel class of somatostatin analogs which are antagonists to somatostatin receptors.

SUMMARY OF THE INVENTION

The invention features a compound of the formula:

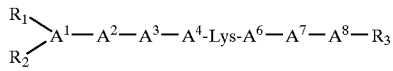

wherein $A^1$ is a D- or L-isomer of an aromatic amino acid, or is deleted;

$A^2$ is a D-isomer selected from the group consisting of Cys, Pen, an aromatic amino acid, or an aliphatic amino acid;

$A^3$ is an aromatic amino acid;

$A^4$ is Trp or D-Trp;

$A^6$ is Thr, Thr(Bzl), Gly, Ser, an Eaa, or an aliphatic amino acid;

$A^7$ is Cys, Pen, or an aromatjkic or an aliphatic amino acid;

$A^8$ is a D- or L-isomer selected from the group consisting of Thr, Ser, an aromatic amino acid, or an aliphatic amino acid;

each of $R_1$ and $R_2$, is, independently, H or substituted (e.g., one to four times) or unsubstituted lower alkyl, aryl, aryl lower alkyl, heterocycle, heterocycle lower alkyl, $E_1SO_2$ or $E_1CO$ (where $E_1$ is aryl, aryl lower alkyl, heterocycle, or heterocycle lower alkyl), where said substituent is halo, lower alkyl, hydroxy, halo lower alkyl, or hydroxy lower alkyl; and $R_3$ is OH, $NH_2$, $C_{1-12}$ alkoxy, or NH—Y—CH$_2$—Z, wherein Y is a $C_{1-12}$ hydrocarbon moiety and Z is H, OH, $CO_2H$, or $CONH_2$, or $R_3$, together with the carbonyl group of $A^8$ attached thereto, are reduced to form H, lower alkyl, or hydroxy lower alkyl; provided if $A^2$ is D-Cys or D-Pen, and $A^7$ is Cys or Pen, then a disulfide bond links the sidechains of $A^2$ and $A^7$, and if $A^1$ is D-Phe or p-NO$_2$-Phe; $A^2$ is D-Cys; $A^3$ is Phe or Tyr; $A^6$ is Thr or Val; and $A^7$ is Cys; then $A^8$ is β-Nal.

In one embodiment, $A^2$ is D-Cys, $A^7$ is Cys, and $A^4$ is D-Trp. In a further embodiment, $A^1$ is an L-aromatic amino acid. In still a further embodiment, $A^1$ and $A^3$, independently, is β-Nal, o-X-Phe (where X is H, OH, CH$_3$, halo, OCH$_3$, NH$_2$, CN, or NO$_2$), p-X-Phe (where X is H, OH, CH$_3$, halo, OCH$_3$, NH$_2$, CN, or NO$_2$), m-X-Phe (where X is H, OH, CH$_3$, halo, OCH$_3$, NH$_2$, CN, or NO$_2$), F$_5$-Phe, Trp, Dip, 2-Pal, Tyr(Bzl), His, Igl, Tyr(I), Bta, Bip, Npa, or Pal; $A^6$ is Thr, Ser, Tle, Thr(Bzl), Abu, Ala, Ile, Leu, Gly, Nle, β-Ala, Gaba, or Val; and $A^8$ is the D- or L-isomer of Thr, Dip, F$_5$-Phe, p-X-Phe (where X is H, OH, CH$_3$, halo, OCH$_3$, NH$_2$, CN, or NO$_2$), o-X-Phe (where X is H, OH, CH$_3$, halo, OCH$_3$, NH$_2$, CN, or NO$_2$), m-X-Phe (where X is H, OH, CH$_3$, halo, OCH$_3$, NH$_2$, CN, or NO$_2$), Igl, Tyr(Bzl), or β-Nal. In yet still another embodiment, $A^1$ is β-Nal, Npa, Igl, Phe, p-F-Phe, Trp, p-Cl-Phe, or p-CN-Phe; $A^3$ is Tyr, Tyr(I), or Pal; $A^6$ is Val, Tle, Nle, Ile, or Leu; $A^8$ is p-F-Phe, β-Nal, Tyr, Dip, p-Cl-Phe, Igl, or p-CN-Phe; $R_1$ is H, CH$_3$CO, 4-(2-hydroxyethyl)-1-piperazinylacetyl, or 4-(2-hydroxyethyl)-1-piperizineethanesulfonyl; $R_2$ is H; and $R_3$ is $NH_2$.

In another further embodiment, $A^1$ is a D-aromatic amino acid. In still another further embodiment, $A^1$ is D-β-Nal, D-o-X-Phe (where X is H, OH, CH$_3$, halo, OCH$_3$, NH$_2$, CN, or NO$_2$), D-p-X-Phe (where X is H, OH, CH$_3$, halo, OCH$_3$, NH$_2$, CN, or NO$_2$), D-m-X-Phe (where X is H, OH, CH$_3$, halo, OCH$_3$, NH$_2$, CN, or NO$_2$), D-F$_5$-Phe, D-Trp, D-Dip, D-2-Pal, D-Tyr(Bzl), D-His, D-Igl, D-Tyr(I), D-Bta, D-Bip, D-Npa, or D-Pal; $A^3$ is β-Nal, o-X-Phe (where X is H, OH, CH$_3$, halo, OCH$_3$, NH$_2$, CN, or NO$_2$), p-X-Phe (where X is H, OH, CH$_3$, halo, OCH$_3$, NH$_2$, CN, or NO$_2$), m-X-Phe (where X is H, OH, CH$_3$, halo, OCH$_3$, NH$_2$, CN, or NO$_2$), F$_5$-Phe, Trp, Dip, 2-Pal, Tyr(Bzl), His, Igl, Tyr(I), Bta, Bip, Npa, or Pal; $A^6$ is Thr, Ser, Tle, Thr(Bzl), Abu, Ala, Ile, Leu, Gly, Nle, β-Ala, Gaba, or Val; and $A^8$ is the D- or L-isomer of Thr, Dip, F$_5$-Phe, p-X-Phe (where X is H, OH, CH$_3$, halo, OCH$_3$, NH$_2$, CN, or NO$_2$), o-X-Phe (where X is H, OH, CH$_3$, halo, OCH$_3$, NH$_2$, CN, or NO$_2$), m-X-Phe (where X is H, OH, CH$_3$, halo, OCH$_3$, NH$_2$, CN, or NO$_2$), Tyr(Bzl), Igl, or β-Nal. In yet still a further embodiment, $A^1$ is D-β-Nal, D-Npa, D-Igl, D-Phe, D-p-F-Phe, D-Trp, D-p-Cl-Phe, or D-p-CN-Phe; $A^3$ is Tyr, Tyr(I), or Pal; $A^6$ is Val, Tle, Nle, Ile, or Leu; $A^8$ is p-F-Phe, β-Nal, Tyr, Dip, p-Cl-Phe, Igl, or p-CN-Phe; $R_1$ is H, CH$_3$CO, 4-(2-hydroxyethyl)-1-piperazinylacetyl, or 4-(2-hydroxyethyl)-1-piperizineethanesulfonyl; $R_2$ is H; and $R_3$ is $NH_2$.

In still another further embodiment, $A^1$ is deleted, $R^1$ is substituted or unsubstituted $E_1CO$, and $R_2$ is H. In still a further embodiment, $R_1$ is substituted or unsubstituted $E_1CO$ (where $E_1$ is phenyl, β-naphthylmethyl, β-pyridinylmethyl, or 3-indolylmethyl); $A^3$ is β-Nal, o-X-Phe (where X is H, OH, CH$_3$, halo, OCH$_3$, NH$_2$, CN, or NO$_2$), p-X-Phe (where X is H, OH, CH$_3$, halo, OCH$_3$, NH$_2$, CN, or NO$_2$), m-X-Phe (where X is H, OH, CH$_3$, halo, OCH$_3$, NH$_2$, CN, or NO$_2$), F$_5$-Phe, Trp, Dip, 2-Pal, Tyr(Bzl), His, Igl, Tyr(I), Bta, Bip, Npa, or Pal; $A^6$ is Thr, Ser, Tle, Thr(Bzl), Abu, Ala, Ile, Leu, Gly, Nle, β-Ala, Gaba, or Val; and $A^8$ is the D- or L-isomer of Thr, Dip, F$_5$-Phe, p-X-Phe (where X is H, OH, CH$_3$, halo, OCH$_3$, NH$_2$, CN, or NO$_2$), o-X-Phe (where X is H, OH, CH$_3$, halo, OCH$_3$, NH$_2$, CN, or NO$_2$), m-X-Phe (where X is H, OH, CH$_3$, halo, OCH$_3$, NH$_2$, CN, or NO$_2$), Igl, Tyr(Bzl), or β-Nal. In yet still a further embodiment, R$_1$ is E$_1$CO (where E$_1$ is 4-hydroxy-phenyl, β-naphthylmethyl, or phenyl); A$^3$ is Tyr, Tyr(I), or Pal; A$^6$ is Val, Tle, Nle, Ile, or Leu; A$^8$ is p-F-Phe, β-Nal, Tyr, Dip, p-Cl-Phe, Igl, or p-CN-Phe; R$_3$ is NH$_2$.

In yet still a further embodiment, R$_3$, together with the carbonyl group of A$^8$ attached thereto, are reduced to form H, lower alkyl, or hydroxy lower alkyl. In still another further embodiment, A$^1$ is the D- or L-isomer of β-Nal, o-X-Phe (where X is H, OH, CH$_3$, halo, OCH$_3$, NH$_2$, CN, or NO$_2$), p-X-Phe (where X is H, OH, CH$_3$, halo, OCH$_3$, NH$_2$, CN, or NO$_2$), m-X-Phe (where X is H, OH, CH$_3$, halo, OCH$_3$, NH$_2$, CN, or NO$_2$), F$_5$-Phe, Trp, Dip, 2-Pal, Tyr(Bzl), His, Igl, Tyr(I), Bta, Bip, Npa, or Pal; A$^3$ is β-Nal, o-X-Phe (where X is H, OH, CH$_3$, halo, OCH$_3$, NH$_2$, CN, or NO$_2$), p-X-Phe (where X is H, OH, CH$_3$, halo, OCH$_3$, NH$_2$, CN, or NO$_2$), m-X-Phe (where X is H, OH, CH$_3$, halo, OCH$_3$, NH$_2$, CN, or NO$_2$), F$_5$-Phe, Trp, Dip, 2-Pal, Tyr(Bzl), His, Igl, Tyr(I), Bta, Bip, Npa, or Pal; A$^6$ is Thr, Ser, Tle, Thr(Bzl), Abu, Ala, Ile, Leu, Gly, Nle, β-Ala, Gaba, or Val; and A$^8$ is the D- or L-isomer of Thr, Dip, F$_5$-Phe, p-X-Phe (where X is H, OH, CH$_3$, halo, OCH$_3$, NH$_2$, CN, or NO$_2$), o-X-Phe (where X is H, OH, CH$_3$, halo, OCH$_3$, NH$_2$, CN, or NO$_2$), m-X-Phe (where X is H, OH, CH$_3$, halo, OCH$_3$, NH$_2$, CN, or NO$_2$), Igl, Tyr(Bzl), or β-Nal. In yet still another further embodiment, A$^1$ is the D- or L-isomer of β-Nal, Phe, p-F-Phe, Trp, p-Cl-Phe, or p-CN-Phe; A$^3$ is Tyr, Tyr(I), or Pal; A$^6$ is Val, Tle, Nle, Ile, or Leu; A$^8$ is p-F-Phe, β-Nal, Tyr, Dip, p-Cl-Phe, Igl, or p-CN-Phe; R$_1$ is H, CH$_3$CO, 4-(2-hydroxyethyl)-1-piperazinylacetyl, or 4-(2-hydroxyethyl)-1-piperizineethanesulfonyl; R$_2$ is H, and R$_3$, together with the carboxy group of A$^8$ attached thereto, are reduced to form H or CH$_3$OH.

In another embodiment, A$^2$ is a D-aromatic amino acid or a D-aliphatic amino acid, A$^7$ is an aromatic amino acid or an aliphatic amino acid, and A$^4$ is D-Trp. In a further embodiment, A$^1$ is an L-amino acid and A$^2$ is a D-aromatic amino acid. In still a further embodiment, A$^1$, A$^3$, and A$^7$ independently, is β-Nal, o-X-Phe (where X is H, OH, CH$_3$, halo, OCH$_3$, NH$_2$, CN, or NO$_2$), p-X-Phe (where X is H, OH, CH$_3$, halo, OCH$_3$, NH$_2$, CN, or NO$_2$), m-X-Phe (where X is H, OH, CH$_3$, halo, OCH$_3$, NH$_2$, CN, or NO$_2$), F$_5$-Phe, Trp, Dip, 2-Pal, Tyr(Bzl), His, Igl, Tyr(I), Bta, Bip, Npa, or Pal; A$^2$ is D-β-Nal, D-o-X-Phe (where X is H, OH, CH$_3$, halo, OCH$_3$, NH$_2$, CN, or NO$_2$), D-p-X-Phe (where X is H, OH, CH$_3$, halo, OCH$_3$, NH$_2$, CN, or NO$_2$), D-m-X-Phe (where X is H, OH, CH$_3$, halo, OCH$_3$, NH$_2$, CN, or NO$_2$), D-F$_5$-Phe, D-Trp, D-Dip, D-2-Pal, D-Tyr(Bzl), D-His, D-Igl, D-Tyr(I), D-Bta, D-Bip, D-Npa, or D-Pal; A$^6$ is Thr, Ser, Tle, Thr(Bzl), Abu, Ala, Ile, Leu, Gly, Nle, β-Ala, Gaba, or Val; and A$^8$ is the D- or L-isomer of Thr, Dip, F$_5$-Phe, p-X-Phe (where X is H, OH, CH$_3$, halo, OCH$_3$, NH$_2$, CN, or NO$_2$), o-X-Phe (where X is H, OH, CH$_3$, halo, OCH$_3$, NH$_2$, CN, or NO$_2$), m-X-Phe (where X is H, OH, CH$_3$, halo, OCH$_3$, NH$_2$, CN, or NO$_2$), Tyr(Bzl), Igl, or β-Nal. In yet still a further embodiment, A$^1$ is β-Nal or Phe, A$^2$ is D-Cpa or D-Phe; A$^3$ is Phe or Tyr; A$^6$ is Abu, Thr, or Val; A$^7$ is Phe; and A$^8$ is Thr; R$_1$ is H, CH$_3$CO, 4-(2-hydroxyethyl)-1-piperazinylacetyl, or 4-(2-hydroxyethyl)-1-piperizineethanesulfonyl; R$_2$ is H; and R$_3$ is NH$_2$.

In another further embodiment, A$^1$ is a D-amino acid and A$^2$ is a D-aromatic amino acid. In still a further embodiment, A$^1$ and A$^2$, independently, is D-β-Nal, D-o-X-Phe (where X is H, OH, CH$_3$, halo, OCH$_3$, NH$_2$, CN, or NO$_2$), D-p-X-Phe (where X is H, OH, CH$_3$, halo, OCH$_3$, NH$_2$, CN, or NO$_2$), D-m-X-Phe (where X is H, OH, CH$_3$, halo, OCH$_3$, NH$_2$, CN, or NO$_2$), D-F$_5$-Phe, D-Trp, D-Dip, D-2-Pal, D-Tyr(Bzl), D-His, D-Igl, D-Tyr(I), D-Bta, D-Bip, D-Npa, or D-Pal; A$^3$ and A$^7$, independently, is β-Nal, o-X-Phe (where X is H, OH, CH$_3$, halo, OCH$_3$, NH$_2$, CN, or NO$_2$), p-X-Phe (where X is H, OH, CH$_3$, halo, OCH$_3$, NH$_2$, CN, or NO$_2$), m-X-Phe (where X is H, OH, CH$_3$, halo, OCH$_3$, NH$_2$, CN, or NO$_2$), F$_5$-Phe, Trp, Dip, 2-Pal, His, Igl, Tyr(I), Bta, Bip, Npa, Tyr(Bzl), or Pal; A$^6$ is Thr, Ser, Tle, Thr(Bzl), Abu, Ala, Ile, Leu, Gly, Nle, β-Ala, Gaba, or Val; and A$^8$ is the D- or L-isomer of Thr, Dip, F$_5$-Phe, p-X-Phe (where X is H, OH, CH$_3$, halo, OCH$_3$, NH$_2$, CN, or NO$_2$), o-X-Phe (where X is H, OH, CH$_3$, halo, OCH$_3$, NH$_2$, CN, or NO$_2$), m-X-Phe (where X is H, OH, CH$_3$, halo, OCH$_3$, NH$_2$, CN, or NO$_2$), Igl, Tyr(Bzl), or β-Nal. In yet still a further embodiment, A$^1$ is D-β-Nal or D-Phe; A$^2$ is D-Cpa or D-Phe; A$^3$ is Phe or Tyr; A$^6$ is Thr or Val; A$^7$ is Phe; and A$^8$ is Thr; R$_1$ is H, CH$_3$CO, 4-(2-hydroxyethyl)-1-piperazinylacetyl, or 4-(2-hydroxyethyl)-1-piperizineethanesulfonyl; R$_2$ is H; and R$_3$ is NH$_2$.

Examples of compounds of the present invention include the following:

H$_2$-β-Nal-D-Cys-Tyr-D-Trp-Lys-Val-Cys-β-Nal-NH$_2$ (Analog No. 2);

(H) (CH$_3$CO)-β-Nal-D-Cys-Tyr-D-Trp-Lys-Val-Cys-β-Nal-NH$_2$ (Analog No. 5);

(H)-(4-(2-hydroxyethyl)-1-piperazinylacetyl)-β-Nal-D-Cys-Tyr-D-Trp-Lys-Val-Cys-β-Nal-NH$_2$;

(H)-(4-(2-hydroxyethyl)-1-piperizineethanesulfonyl)-β-Nal-D-Cys-Tyr-D-Trp-Lys-Val-Cys-β-Nal-NH$_2$;

H$_2$-β-Nal-D-Cys-Pal-D-Trp-Lys-Val-Cys-β-Nal-NH$_2$ (Analog No.3);

(H) (CH$_3$CO)-β-Nal-D-Cys-Pal-D-Trp-Lys-Val-Cys-β-Nal-NH$_2$;

(H)-(4-(2-hydroxyethyl)-1-piperazinylacetyl)-β-Nal-D-Cys-Pal-D-Trp-Lys-Val-Cys-β-Nal-NH$_2$;

(H)-(4-(2-hydroxyethyl)-1-piperizineethanesulfonyl)-β-Nal-D-Cys-Pal-D-Trp-Lys-Val-Cys-β-Nal-NH$_2$;

H$_2$-β-Nal-D-Cys-Tyr-D-Trp-Lys-Val-Cys-Thr-NH$_2$;

(H) (CH$_3$CO)-β-Nal-D-Cys-Tyr-D-Trp-Lys-Val-Cys-Thr-NH$_2$;

(H) (4-(2-hydroxyethyl)-1-piperazinylacetyl)-β-Nal-D-Cys-Tyr-D-Trp-Lys-Val-Cys-Thr-NH$_2$;

(H) (4-(2-hydroxyethyl)-1-piperizineethanesulfonyl)-β-Nal-D-Cys-Tyr-D-Trp-Lys-Val-Cys-Thr-NH$_2$;

H$_2$-β-Nal-D-Cys-Pal-D-Trp-Lys-Val-Cys-Thr-NH$_2$;

(H) (CH$_3$CO)-β-Nal-D-Cys-Pal-D-Trp-Lys-Val-Cys-Thr-NH$_2$;

(H) (4-(2-hydroxyethyl)-1-piperazinylacetyl)-β-Nal-D-Cys-Pal-D-Trp-Lys-Val-Cys-Thr-NH$_2$;

(H) (4-(2-hydroxyethyl)-1-piperizineethanesulfonyl)-β-Nal-D-Cys-Pal-D-Trp-Lys-Val-Cys-Thr-NH$_2$;

H$_2$-Phe-D-Cys-Tyr-D-Trp-Lys-Val-Cys-β-Nal-NH$_2$;

(H) (CH$_3$CO)Phe-D-Cys-Tyr-D-Trp-Lys-Val-Cys-β-Nal-NH$_2$;

(H) (4-(2-hydroxyethyl)-1-piperazinylacetyl)-Phe-D-Cys-Tyr-D-Trp-Lys-Val-Cys-β-Nal-NH$_2$;

(H) (4-(2-hydroxyethyl)-1-piperizineethanesulfonyl)-Phe-D-Cys-Tyr-D-Trp-Lys-Val-Cys-β-Nal-NH$_2$;

H$_2$-Phe-D-Cys-Pal-D-Trp-Lys-Val-Cys-β-Nal-NH$_2$ (Analog No. 4);

(H) (CH$_3$CO)Phe-D-Cys-Pal-D-Trp-Lys-Val-Cys-β-Nal-NH$_2$;

(H) (4-(2-hydroxyethyl)-1-piperazinylacetyl)-Phe-D-Cys-Pal-D-Trp-Lys-Val-Cys-β-Nal-NH$_2$;

(H) (4-(2-hydroxyethyl)-1-piperizineethanesulfonyl)-Phe-D-Cys-Pal-D-Trp-Lys-Val-Cys-β-Nal-NH$_2$;

H$_2$-Phe-D-Cys-Pal-D-Trp-Lys-Val-Cys-Thr-NH$_2$;

(H) (CH$_3$CO)-Phe-D-Cys-Pal-D-Trp-Lys-Val-Cys-Thr-NH$_2$;

(H) (4-(2-hydroxyethyl)-1-piperazinylacetyl)-Phe-D-Cys-Pal-D-Trp-Lys-Val-Cys-Thr-NH$_2$;

(H) (4-(2-hydroxyethyl)-1-piperizineethanesulfonyl)-Phe-D-Cys-Pal-D-Trp-Lys-Val-Cys-Thr-NH$_2$;

H$_2$-β-Nal-D-Cys-Tyr-D-Trp-Lys-Thr-Cys-β-Nal-NH$_2$;

(H) (CH$_3$CO)-β-Nal-D-Cys-Pal-D-Trp-Lys-Thr-Cys-β-Nal-NH$_2$;

(H) (4-(2-hydroxyethyl)-1-piperazinylacetyl)-β-Nal-D-Cys-Tyr-D-Trp-Lys-Thr-Cys-β-Nal-NH$_2$;

(H) (4-(2-hydroxyethyl)-1-piperizineethanesulfonyl)-β-Nal-D-Cys-Tyr-D-Trp-Lys-Thr-Cys-β-Nal-NH$_2$;

H$_2$-β-Nal-D-Cys-Pal-D-Trp-Lys-Thr-Cys-β-Nal-NH$_2$;

(H) (CH$_3$CO)-β-Nal-D-Cys-Pal-D-Trp-Lys-Thr-Cys-β-Nal-NH$_2$;

(H) (4-(2-hydroxyethyl)-1-piperazinylacetyl)-β-Nal-D-Cys-Pal-D-Trp-Lys-Thr-Cys-β-Nal-NH$_2$;

(H) (4-(2-hydroxyethyl)-1-piperizineethanesulfonyl)-β-Nal-D-Cys-Pal-D-Trp-Lys-Thr-Cys-β-Nal-NH$_2$;

H$_2$-β-Nal-D-Cys-Tyr-D-Trp-Lys-Thr-Cys-Thr-NH$_2$;

H(CH$_3$CO)-β-Nal-D-Cys-Tyr-D-Trp-Lys-Thr-Cys-Thr-NH$_2$;

(H) (4-(2-hydroxyethyl)-1-piperazinylacetyl)-β-Nal-D-Cys-Tyr-D-Trp-Lys-Thr-Cys-Thr-NH$_2$;

(H) (4-(2-hydroxyethyl)-1-piperizineethanesulfonyl)-β-Nal-D-Cys-Tyr-D-Trp-Lys-Thr-Cys-Thr-NH$_2$;

H$_2$-β-Nal-D-Cys-Pal-D-Trp-Lys-Thr-Cys-Thr-NH$_2$;

(H) (CH$_3$CO)-β-Nal-D-Cys-Pal-D-Trp-Lys-Thr-Cys-Thr-NH$_2$;

(H) (4-(2-hydroxyethyl)-1-piperazinylacetyl)-β-Nal-D-Cys-Pal-D-Trp-Lys-Thr-Cys-Thr-NH$_2$;

(H) (4-(2-hydroxyethyl)-1-piperizineethanesulfonyl)-β-Nal-D-Cys-Pal-D-Trp-Lys-Thr-Cys-Thr-NH$_2$;

H$_2$-Phe-D-Cys-Tyr-D-Trp-Lys-Thr-Cys-β-Nal-NH$_2$;

(H) (CH$_3$CO)Phe-D-Cys-Tyr-D-Trp-Lys-Thr-Cys-β-Nal-NH$_2$;

(H) (4-(2-hydroxyethyl)-1-piperazinylacetyl)Phe-D-Cys-Tyr-D-Trp-Lys-Thr-Cys-β-Nal-NH$_2$;

(H) (4-(2-hydroxyethyl)-1-piperizineethanesulfonyl)Phe-D-Cys-Tyr-D-Trp-Lys-Thr-Cys-β-Nal-NH$_2$;

H$_2$-Phe-D-Cys-Pal-D-Trp-Lys-Thr-Cys-β-Nal-NH$_2$;

(H) (CH$_3$CO)Phe-D-Cys-Pal-D-Trp-Lys-Thr-Cys-β-Nal-NH$_2$;

(H) (4-(2-hydroxyethyl)-1-piperazinylacetyl)Phe-D-Cys-Pal-D-Trp-Lys-Thr-Cys-β-Nal-NH$_2$;

(H) (4-(2-hydroxyethyl)-1-piperizineethanesulfonyl)Phe-D-Cys-Pal-D-Trp-Lys-Thr-Cys-β-Nal-NH$_2$;

H$_2$-Phe-D-Cys-Tyr-D-Trp-Lys-Thr-Cys-Thr-NH$_2$;

(H) (CH$_3$CO)Phe-D-Cys-Tyr-D-Trp-Lys-Thr-Cys-Thr-NH$_2$;

(H) (4-(2-hydroxyethyl)-1-piperazinylacetyl)Phe-D-Cys-Tyr-D-Trp-Lys-Thr-Cys-Thr-NH$_2$;

(H) (4-(2-hydroxyethyl)-1-piperizineethanesulfonyl)Phe-D-Cys-Tyr-D-Trp-Lys-Thr-Cys-Thr-NH$_2$;

H$_2$-Phe-D-Cys-Pal-D-Trp-Lys-Thr-Cys-Thr-NH$_2$ (Analog No. 6);

(H) (CH$_3$CO)-Phe-D-Cys-Pal-D-Trp-Lys-Thr-Cys-Thr-NH$_2$;

(H) (4-(2-hydroxyethyl)-1-piperazinylacetyl)Phe-D-Cys-Pal-D-Trp-Lys-Thr-Cys-Thr-NH$_2$;

(H) (4-(2-hydroxyethyl)-1-piperizineethanesulfonyl)Phe-D-Cys-Pal-D-Trp-Lys-Thr-Cys-Thr-NH$_2$;

H$_2$-β-Nal-D-Cys-Tyr-D-Trp-Lys-Abu-Cys-β-Nal-NH$_2$;

H$_2$-Phe-D-Cys-Tyr-D-Trp-Lys-Abu-Cys-β-Nal-NH$_2$;

H$_2$-β-Nal-D-Cys-Pal-D-Trp-Lys-Abu-Cys-β-Nal-NH$_2$;

H$_2$-Phe-D-Cys-Pal-D-Trp-Lys-Abu-Cys-β-Nal-NH$_2$;

H$_2$-β-Nal-D-Cys-Tyr-D-Trp-Lys-Abu-Cys-Thr-NH$_2$;

H$_2$-Phe-D-Pen-Tyr-D-Trp-Lys-Val-Pen-β-Nal-NH$_2$; or

H$_2$-Phe-D-Pen-Pal-D-Trp-Lys-Thr-Pen-Thr-NH$_2$;

H$_2$-Dip-D-Cys-Pal-D-Trp-Lys-Val-Cys-Dip-NH$_2$ (Analog No. 10);

H$_2$-F$_5$-Phe-D-Cys-His-D-Trp-Lys-Val-Cys-F$_5$-Phe-NH$_2$ (Analog No. 11);

H$_2$-Dip-D-Cys-Pal-D-Trp-Lys-Val-Cys-β-Nal-NH$_2$ (Analog No. 13);

H$_2$-m-F-Phe-D-Cys-Pal-D-Trp-Lys-Val-Cys-m-F-Phe-NH$_2$ (Analog No. 14);

H$_2$-o-F-Phe-D-Cys-Pal-D-Trp-Lys-Val-Cys-o-F-Phe-NH$_2$ (Analog No. 15);

H$_2$-p-F-Phe-D-Cys-Pal-D-Trp-Lys-Val-Cys-p-F-Phe-NH$_2$ (Analog No. 12);

H$_2$-F$_5$-Phe-D-Cys-Pal-D-Trp-Lys-Val-Cys-F$_5$-Phe-NH$_2$ (Analog No. 16);

H$_2$-F$_5$-Phe-D-Cys-2-Pal-D-Trp-Lys-Val-Cys-F$_5$-Phe-NH$_2$ (Analog No. 17);

H$_2$-β-Nal-D-Cys-His-D-Trp-Lys-Val-Cys-D-Dip-NH$_2$ (Analog No. 19);

H$_2$-Dip-D-Cys-His-D-Trp-Lys-Val-Cys-β-Nal-NH$_2$ (Analog No. 20);

H$_2$-Dip-D-Cys-His-D-Trp-Lys-Val-Cys-Dip-NH$_2$ (Analog No. 21);

H$_2$-β-Nal-D-Cys-His-D-Trp-Lys-Val-Cys-β-Nal-NH$_2$ (Analog No. 22);

H$_2$-Trp-D-Cys-Tyr-D-Trp-Lys-Val-Cys-D-β-Nal-NH$_2$ (Analog No. 24);

H$_2$-β-Nal-D-Cys-Tyr-D-Trp-Lys-Val-Cys-D-β-Nal-NH$_2$ (Analog No. 25);

H$_2$-β-Nal-D-Cys-Pal-D-Trp-Lys-Val-Cys-D-p-F-Phe-NH$_2$ (Analog No. 28);

H$_2$-β-Nal-D-Cys-Pal-D-Trp-Lys-Tle-Cys-β-Nal-NH$_2$ (Analog No. 29);

H$_2$-p-F-Phe-D-Cys-Pal-D-Trp-Lys-Val-Cys-β-Nal-NH$_2$ (Analog No. 30);

H$_2$-β-Nal-D-Cys-Pal-D-Trp-Lys-Nle-Cys-β-Nal-NH$_2$ (Analog No. 31);

H$_2$-β-Nal-D-Cys-Pal-D-Trp-Lys-Ile-Cys-β-Nal-NH$_2$ (Analog No. 32);

H$_2$-β-Nal-D-Cys-Pal-D-Trp-Lys-Gly-Cys-β-Nal-NH$_2$ (Analog No. 33);

H$_2$-β-Nal-D-Cys-Pal-D-Trp-Lys-Ala-Cys-β-Nal-NH$_2$ (Analog No. 34);

H$_2$-β-Nal-D-Cys-Pal-D-Trp-Lys-Leu-Cys-β-Nal-NH$_2$ (Analog No. 35);

H$_2$-Bip-D-Cys-Tyr-D-Trp-Lys-Ile-Cys-Bip-NH$_2$ (Analog No. 36);

H$_2$-p-F-Phe-D-Cys-His-D-Trp-Lys-Val-Cys-p-F-Phe-NH$_2$ (Analog No. 38);

H$_2$-Npa-D-Cys-Pal-D-Trp-Lys-Val-Cys-Tyr-NH$_2$ (Analog No. 39);

H$_2$-m-F-Phe-D-Cys-His-D-Trp-Lys-Val-Cys-m-F-Phe-NH$_2$ (Analog No. 40);

H$_2$-o-F-Phe-D-Cys-His-D-Trp-Lys-Val-Cys-o-F-Phe-NH$_2$ (Analog No. 41);

H$_2$-β-Nal-D-Cys-Pal-D-Trp-Lys-Val-Cys-Dip-NH$_2$ (Analog No. 42);

H$_2$-Cpa-D-Cys-Pal-D-Trp-Lys-Val-Cys-Cpa-NH$_2$ (Analog No. 43);

H$_2$-Igl-D-Cys-Pal-D-Trp-Lys-Val-Cys-Igl-NH$_2$ (Analog No. 44);

H$_2$-β-Nal-D-Cys-Pal-D-Trp-Lys-Val-Cys-D-Dip-NH$_2$ (Analog No. 45);

H$_2$-β-Nal-D-Cys-3-I-Tyr-D-Trp-Lys-Val-Cys-β-Nal-NH$_2$ (Analog No. 46);

H$_2$-p-CN-Phe-D-Cys-Pal-D-Trp-Lys-Val-Cys-p-CN-Phe-NH$_2$ (Analog No. 47);

H$_2$-β-Nal-D-Cys-Tyr-D-Trp-Lys-Val-Cys-D-Dip-NH$_2$ (Analog No. 48);

H$_2$-β-Nal-D-Cys-Bta-D-Trp-Lys-Val-Cys-β-Nal-NH$_2$ (Analog No. 49);

H$_2$-p-F-Phe-D-Cys-Pal-D-Trp-Lys-Tle-Cys-β-Nal-NH$_2$ (Analog No. 50);

H$_2$-Bpa-D-Cys-Pal-D-Trp-Lys-Val-Cys-Bpa-NH$_2$ (Analog No. 52);

H$_2$-Iph-D-Cys-Pal-D-Trp-Lys-Val-Cys-Iph-NH$_2$ (Analog No. 53);

H$_2$-Trp-D-Cys-Pal-D-Trp-Lys-Tle-Cys-β-Nal-NH$_2$ (Analog No. 54);

H$_2$-p-Cl-Phe-D-Cys-Pal-D-Trp-Lys-Val-Cys-β-Nal-NH$_2$ (Analog No. 55);

H$_2$-p-Cl-Phe-D-Cys-Pal-D-Trp-Lys-Tle-Cys-β-Nal-NH$_2$ (Analog No. 56);

H$_2$-p-Cl-Phe-D-Cys-Pal-D-Trp-Lys-Tle-Cys-p-Cl-Phe-NH$_2$ (Analog No. 57);

H$_2$-p-Cl-Phe-D-Cys-Pal-D-Trp-Lys-Cha-Cys-p-Cl-Phe-NH$_2$;

H$_2$-p-Cl-Phe-D-Cys-Tyr(I)-D-Trp-Lys-Val-Cys-p-Cl-Phe-NH$_2$;

H$_2$-p-Cl-Phe-D-Cys-Tyr(I)-D-Trp-Lys-Val-Cys-β-Nal-NH$_2$;

H$_2$-p-Cl-Phe-D-Cys-Tyr(I)-D-Trp-Lys-Tle-Cys-β-Nal-NH$_2$;

H$_2$-p-F-Phe-D-Cys-Tyr(I)-D-Trp-Lys-Val-Cys-β-Nal-NH$_2$;

H$_2$-p-F-Phe-D-Cys-Tyr(I)-D-Trp-Lys-Tle-Cys-β-Nal-NH$_2$;

H$_2$-β-Nal-D-Cys-Tyr-D-Trp-Lys-Abu-Cys-β-Nal-NH$_2$;

(H) (CH$_3$CO)-β-Nal-D-Cys-Tyr-D-Trp-Lys-Abu-Cys-β-Nal-NH$_2$;

H$_2$-p-NO$_2$-Phe-D-Cys-Tyr-D-Trp-Lys-Abu-Cys-β-Nal-NH$_2$;

(H) (CH$_3$CO)-p-NO$_2$-Phe-D-Cys-Tyr-D-Trp-Lys-Abu-Cys-β-Nal-NH$_2$;

H$_2$-p-NO$_2$-Phe-D-Cys-Tyr(Bzl)-D-Trp-Lys-Thr(Bzl)-Cys-β-Nal-NH$_2$;

(H) (4-(2-hydroxyethyl)-1-piperazinylacetyl)-p-NO$_2$-Phe-D-Cys-Tyr(Bzl)-D-Trp-Lys-Thr(Bzl)-Cys-β-Nal-NH$_2$;

(H) (4-(2-hydroxyethyl)-1-piperazinylacetyl)-p-NO$_2$-Phe-D-Cys-Tyr-D-Trp-Lys-Thr-Cys-Tyr-NH$_2$;

H$_2$-p-NO$_2$-Phe-D-Cys-Tyr-D-Trp-Lys-Val-Cys-β-Nal-NH$_2$;

(H) (4-(2-hydroxyethyl)-1-piperazinylacetyl)-p-NO$_2$-Phe-D-Cys-Tyr-D-Trp-Lys-Val-Cys-β-Nal-NH$_2$;

(H) (4-(2-hydroxyethyl)-1-piperazinylacetyl)-β-Nal-Phe-D-Cys-Tyr-D-Trp-Lys-Val-Cys-β-Nal-NH$_2$;

H$_2$-β-Nal-D-Cys-Tyr(Bzl)-D-Trp-Lys-Thr(Bzl)-Cys-β-Nal-NH$_2$;

(H) (4-2-hydroxyethyl)-1-piperazinylacetyl)-β-Nal-D-Cys-Tyr(Bzl)-D-Trp-Lys-Thr(Bzl)-Cys-Tyr(Bzl)-NH$_2$;

H$_2$-D-Phe-D-Pen-Tyr-D-Trp-Lys-Val-Cys-Thr-NH$_2$;

H$_2$-D-β-Nal-D-Cys-Tyr-D-Trp-Lys-Val-Cys-Thr-NH$_2$;

H$_2$-D-β-Nal-D-Cys-Tyr-D-Trp-Lys-Val-Cys-β-Nal-NH$_2$ (Analog No. 9);

H$_2$-D-β-Nal-D-Cys-Tyr-D-Trp-Lys-Thr-Cys-β-Nal-NH$_2$;

H$_2$-D-Phe-D-Cys-Pal-D-Trp-Lys-Thr-Cys-Thr-NH$_2$;

H$_2$-D-Phe-D-Cys-Tyr-D-Trp-Lys-Abu-Cys-Thr-NH$_2$;

H$_2$-D-β-Nal-D-Cys-Tyr-D-Trp-Lys-Abu-Cys-Thr-NH$_2$;

H$_2$-D-β-Nal-D-Cys-Tyr-D-Trp-Lys-Val-Cys-D-β-Nal-NH$_2$ (Analog No. 26);

H$_2$-D-p-F-Phe-D-Cys-Pal-D-Trp-Lys-Val-Cys-D-p-F-Phe-NH$_2$ (Analog No. 27);

H$_2$-D-Bip-D-Cys-Tyr-D-Trp-Lys-Val-Cys-β-Nal-NH$_2$ (Analog No. 37);

H$_2$-D-Dip-D-Cys-Pal-D-Trp-Lys-Val-Cys-β-Nal-NH$_2$ (Analog No. 18);

H$_2$-D-p-F-Phe-D-Cys-Pal-D-Trp-Lys-Tle-Cys-β-Nal-NH$_2$ (Analog No. 51);

H$_2$-D-p-Cl-Phe-D-Cys-Pal-D-Trp-Lys-Tle-Cys-p-Cl-Phe-NH$_2$ (Analog No. 7);

p-NO$_2$-D-Phe-D-Cys-Pal-D-Trp-Lys-Thr(Bzl)-Cys-Tyr(Bzl)-NH$_2$;

p-NO$_2$-D-Phe-D-Cys-Tyr(Bzl)-D-Trp-Lys-Val-Cys-Tyr(Bzl)-NH$_2$;

(H) (4-(2-hydroxyethyl)-1-piperazinylacetyl)-p-NO$_2$-D-Phe-D-Cys-Pal-D-Trp-Lys-Thr(Bzl)-Cys-Tyr(Bzl)-NH$_2$;

(H) (4-(2-hydroxyethyl)-1-piperazinylacetyl)-p-NO$_2$-D-Phe-D-Cys-Tyr(Bzl)-D-Trp-Lys-Val-Cys-Tyr(Bzl)-NH$_2$;

(H) (3-phenylpropionyl)-D-Cys-Tyr-D-Trp-Lys-Val-Cys-β-Nal-NH$_2$;

(H) (3-phenylpropionyl)-D-Cys-Pal-D-Trp-Lys-Val-Cys-β-Nal-NH$_2$;

(H) (3-phenylpropionyl)-D-Cys-Tyr-D-Trp-Lys-Thr-Cys-β-Nal-NH$_2$;

(H) (3-phenylpropionyl)-D-Cys-Pal-D-Trp-Lys-Thr-Cys-β-Nal-NH$_2$;

(H) (3-phenylpropionyl)-D-Cys-Tyr-D-Trp-Lys-Val-Cys-Thr-NH$_2$;

(H) (3-phenylpropionyl)-D-Cys-Pal-D-Trp-Lys-Val-Cys-Thr-NH$_2$;

(H) (3-phenylpropionyl)-D-Cys-Tyr-D-Trp-Lys-Thr-Cys-Thr-NH$_2$;

(H) (3-phenylpropionyl)-D-Cys-Pal-D-Trp-Lys-Thr-Cys-Thr-NH$_2$;

(H) (3-[2-naphthyl]propionyl)-D-Cys-Tyr-D-Trp-Lys-Val-Cys-β-Nal-NH$_2$;

(H) (3-[2-naphthyl]propionyl)-D-Cys-Pal-D-Trp-Lys-Val-Cys-β-Nal-NH$_2$;

(H) (3-[2-naphthyl]propionyl)-D-Cys-Tyr-D-Trp-Lys-Thr-Cys-β-Nal-NH$_2$;

(H) (3-[2-naphthyl]propionyl)-D-Cys-Pal-D-Trp-Lys-Thr-Cys-β-Nal-NH₂;

(H) (3-[2-naphthyl]propionyl)-D-Cys-Tyr-D-Trp-Lys-Val-Cys-Thr-NH₂;

(H) (3-[2-naphthyl]propionyl)-D-Cys-Pal-D-Trp-Lys-Val-Cys-Thr-NH₂;

(H) (3-[2-naphthyl]propionyl)-D-Cys-Tyr-D-Trp-Lys-Thr-Cys-Thr-NH₂;

(H) (3-[2-naphthyl]propionyl)-D-Cys-Pal-D-Trp-Lys-Thr-Cys-Thr-NH₂;

(H) (3-[p-hydroxyphenyl])-D-Cys-Tyr-D-Trp-Lys-Val-Cys-β-Nal-NH₂;

(H) (3-naphthyl]propionyl)-D-Cys-Tyr-D-Trp-Lys-Abu-Cys-β-Nal-NH₂;

(H) (3-naphthyl]propionyl)-D-Cys-Tyr-D-Trp-Lys-Abu-Cys-Thr-NH₂;

(H) (3-phenylylpropionyl)-D-Cys-Tyr-D-Trp-Lys-Abu-Cys-β-Nal-NH₂

(H) (3-phenylylpropionyl)-D-Cys-Tyr-D-Trp-Lys-Abu-Cys-Thr-NH₂;

H₂-β-Nal-D-Cys-Tyr-D-Trp-Lys-Val-Cys-2R,3R-(2-hydroxymethyl)-3-hydroxy)propylamide;

(H) (CH₃CO)-β-Nal-D-Cys-Tyr-D-Trp-Lys-Val-Cys-2R,3R-(2-hydroxymethyl)-3-hydroxy)propylamide;

(H) (4-(2-hydroxyethyl)-1-piperazinylacetyl)-β-Nal-D-Cys-Tyr-D-Trp-Lys-Val-Cys-2R,3R-(2-hydroxymethyl)-3-hydroxy)propylamide;

(H) (4-(2-hydroxyethyl)-1-piperizineethanesulfonyl)-β-Nal-D-Cys-Tyr-D-Trp-Lys-Val-Cys-2R,3R-(2-hydroxymethyl)-3-hydroxy)propylamide;

H₂-β-Nal-D-Cys-Pal-D-Trp-Lys-Val-Cys-2R,3R-(2-hydroxymethyl)-3-hydroxy)propylamide;

(H) (CH₃CO)-β-Nal-D-Cys-Pal-D-Trp-Lys-Val-Cys-2R,3R-(2-hydroxymethyl)-3-hydroxy)propylamide;

(H) (4-(2-hydroxyethyl)-1-piperazinylacetyl)-β-Nal-D-Cys-Pal-D-Trp-Lys-Val-Cys-2R,3R-(2-hydroxymethyl)-3-hydroxy)propylamide;

(H) (4-(2-hydroxyethyl)-1-piperizineethanesulfonyl)-β-Nal-D-Cys-Pal-D-Trp-Lys-Val-Cys-2R,3R-(2-hydroxymethyl)-3-hydroxy)propylamide;

H₂-β-Nal-D-Cys-Tyr-D-Trp-Lys-Thr-Cys-2R,3R-(2-hydroxymethyl)-3-hydroxy)propylamide;

(H) (CH₃CO)-β-Nal-D-Cys-Tyr-D-Trp-Lys-Thr-Cys-2R,3R-(2-hydroxymethyl)-3-hydroxy)propylamide;

(H) (4-(2-hydroxyethyl)-1-piperazinylacetyl)-β-Nal-D-Cys-Tyr-D-Trp-Lys-Thr-Cys-2R,3R-(2-hydroxymethyl)-3-hydroxy)propylamide;

(H) (4-(2-hydroxyethyl)-1-piperizineethanesulfonyl)-β-Nal-D-Cys-Tyr-D-Trp-Lys-Thr-Cys-2R,3R-(2-hydroxymethyl)-3-hydroxy)propylamide;

H₂-β-Nal-D-Cys-Pal-D-Trp-Lys-Thr-Cys-2R,3R-(2-hydroxymethyl)-3-hydroxy)propylamide;

(H) (CH₃CO)-β-Nal-D-Cys-Pal-D-Trp-Lys-Thr-Cys-2R,3R-(2-hydroxymethyl)-3-hydroxy)propylamide;

(H) (4-(2-hydroxyethyl)-1-piperazinylacetyl)-β-Nal-D-Cys-Pal-D-Trp-Lys-Thr-Cys-2R,3R-(2-hydroxymethyl)-3-hydroxy)propylamide;

(H) (4-(2-hydroxyethyl)-1-piperizineethanesulfonyl)-β-Nal-D-Cys-Pal-D-Trp-Lys-Thr-Cys-2R,3R-(2-hydroxymethyl)-3-hydroxy)propylamide;

H₂-Phe-D-Cys-Tyr-D-Trp-Lys-Val-Cys-2R,3R-(2-hydroxymethyl)-3-hydroxy)propylamide;

(H) (CH₃CO)Phe-D-Cys-Tyr-D-Trp-Lys-Val-Cys-2R,3R-(2-hydroxymethyl)-3-hydroxy)propylamide;

(H) (4-(2-hydroxyethyl)-1-piperazinylacetyl)Phe-D-Cys-Tyr-D-Trp-Lys-Val-Cys-2R,3R-(2-hydroxymethyl)-3-hydroxy)propylamide;

(H) (4-(2-hydroxyethyl)-1-piperizineethanesulfonyl)Phe-D-Cys-Tyr-D-Trp-Lys-Val-Cys-2R,3R-(2-hydroxymethyl)-3-hydroxy)propylamide;

H₂-Phe-D-Cys-Pal-D-Trp-Lys-Val-Cys-2R,3R-(2-hydroxymethyl)-3-hydroxy)propylamide;

H(CH₃CO)Phe-D-Cys-Pal-D-Trp-Lys-Val-Cys-2R,3R-(2-hydroxymethyl)-3-hydroxy)propylamide;

(H) (4-(2-hydroxyethyl)-1-piperazinylacetyl)Phe-D-Cys-Pal-D-Trp-Lys-Val-Cys-2R,3R-(2-hydroxymethyl)-3-hydroxy)propylamide;

(H) (4-(2-hydroxyethyl)-1-piperizineethanesulfonyl)Phe-D-Cys-Pal-D-Trp-Lys-Val-Cys-2R,3R-(2-hydroxymethyl)-3-hydroxy)propylamide;

H₂-Phe-D-Cys-Tyr-D-Trp-Lys-Thr-Cys-2R,3R-(2-hydroxymethyl)-3-hydroxy)propylamide;

(H) (CH₃CO)Phe-D-Cys-Tyr-D-Trp-Lys-Thr-Cys-2R,3R-(2-hydroxymethyl)-3-hydroxy)propylamide;

(H) (4-(2-hydroxyethyl)-1-piperazinylacetyl)Phe-D-Cys-Tyr-D-Trp-Lys-Thr-Cys-2R,3R-(2-hydroxymethyl)-3-hydroxy)propylamide;

(H) (4-(2-hydroxyethyl)-1-piperizineethanesulfonyl)Phe-D-Cys-Tyr-D-Trp-Lys-Thr-Cys-2R,3R-(2-hydroxymethyl)-3-hydroxy)propylamide;

H₂-Phe-D-Cys-Pal-D-Trp-Lys-Thr-Cys-2R,3R-(2-hydroxymethyl)-3-hydroxy)propylamide;

(H) (CH₃CO)Phe-D-Cys-Pal-D-Trp-Lys-Thr-Cys-2R,3R-(2-hydroxymethyl)-3-hydroxy)propylamide;

(H) (4-(2-hydroxyethyl)-1-piperazinylacetyl)Phe-D-Cys-Pal-D-Trp-Lys-Thr-Cys-2R,3R-(2-hydroxymethyl)-3-hydroxy)propylamide;

(H) (4-(2-hydroxyethyl)-1-piperizineethanesulfonyl)Phe-D-Cys-Pal-D-Trp-Lys-Thr-Cys-2R,3R-(2-hydroxymethyl)-3-hydroxy)propylamide;

H₂-β-Nal-D-Cys-Tyr-D-Trp-Lys-Val-Cys-2R-(2-naphthyl)ethylamide;

(H) (CH₃CO)-β-Nal-D-Cys-Tyr-D-Trp-Lys-Val-Cys-2R-(2-naphthyl)ethylamide;

(H) (4-(2-hydroxyethyl)-1-piperazinylacetyl)-β-Nal-D-Cys-Tyr-D-Trp-Lys-Val-Cys-2R-(2-naphthyl)ethylamide;

(H) (4-(2-hydroxyethyl)-1-piperizineethanesulfonyl)-β-Nal-D-Cys-Tyr-D-Trp-Lys-Val-Cys-2R-(2-naphthyl)ethylamide;

H₂-β-Nal-D-Cys-Pal-D-Trp-Lys-Val-Cys-2R-(2-naphthyl)ethylamide;

(H) (CH₃CO)-β-Nal-D-Cys-Pal-D-Trp-Lys-Val-Cys-2R-(2-naphthyl)ethylamide;

(H) (4-(2-hydroxyethyl)-1-piperazinylacetyl)-β-Nal-D-Cys-Pal-D-Trp-Lys-Val-Cys-2R-(2-naphthyl)ethylamide;

(H) (4-(2-hydroxyethyl)-1-piperizineethanesulfonyl)-β-Nal-D-Cys-Pal-D-Trp-Lys-Val-Cys-2R-(2-naphthyl)ethylamide;

H₂-β-Nal-D-Cys-Tyr-D-Trp-Lys-Thr-Cys-2R-(2-naphthyl) ethylamide;

(H) (CH₃CO)-β-Nal-D-Cys-Tyr-D-Trp-Lys-Thr-Cys-2R-(2-naphthyl)ethylamide;

(H) (4-(2-hydroxyethyl)-1-piperazinylacetyl)-β-Nal-D-Cys-Tyr-D-Trp-Lys-Thr-Cys-2R-(2-naphthyl)ethylamide;

(H) (4-(2-hydroxyethyl)-1-piperizineethanesulfonyl)-β-Nal-D-Cys-Tyr-D-Trp-Lys-Thr-Cys-2R-(2-naphthyl)ethylamide;

H$_2$-β-Nal-D-Cys-Pal-D-Trp-Lys-Thr-Cys-2R-(2-naphthyl)ethylamide;

(H) (CH$_3$CO)-β-Nal-D-Cys-Pal-D-Trp-Lys-Thr-Cys-2R-(2-naphthyl)ethylamide;

(H) (4-(2-hydroxyethyl)-1-piperazinylacetyl)-β-Nal-D-cys-Pal-D-Trp-Lys-Thr-Cys-2R-(2-naphthyl)ethylamide;

(H) (4-(2-hydroxyethyl)-1-piperizineethanesulfonyl)-β-Nal-D-Cys-Pal-D-Trp-Lys-Thr-Cys-2R-(2-naphthyl)ethylamide;

H$_2$-Phe-D-Cys-Tyr-D-Trp-Lys-Val-Cys-2R-(2-naphthyl)ethylamide;

(H) (CH$_3$CO)Phe-D-Cys-Tyr-D-Trp-Lys-Val-Cys-2R-(2-naphthyl)ethylamide;

(H) (4-(2-hydroxyethyl)-1-piperazinylacetyl)Phe-D-Cys-Tyr-D-Trp-Lys-Val-Cys-2R-(2-naphthyl)ethylamide;

(H) (4-(2-hydroxyethyl)-1-piperizineethanesulfonyl)Phe-D-Cys-Tyr-D-Trp-Lys-Val-Cys-2R-(2-naphthyl)ethylamide;

H$_2$-Phe-D-Cys-Pal-D-Trp-Lys-Val-Cys-2R-(2-naphthyl)ethylamide;

(H) (CH$_3$CO)Phe-Cys-Pal-D-Trp-Lys-Val-Cys-2R-(2-naphthyl)ethylamide;

(H) (4-(2-hydroxyethyl)-1-piperazinylacetyl)Phe-D-Cys-Pal-D-Trp-Lys-Val-Cys-2R-(2-naphthyl)ethylamide;

(H) (4-(2-hydroxyethyl)-1-piperizineethanesulfonyl)Phe-D-Cys-Pal-D-Trp-Lys-Val-Cys-2R-(2-naphthyl)ethylamide;

H$_2$-Phe-D-Cys-Tyr-D-Trp-Lys-Thr-Cys-2R-(2-naphthyl)ethylamide;

(H) (CH$_3$CO)Phe-D-Cys-Tyr-D-Trp-Lys-Thr-Cys-2R-(2-naphthyl)ethylamide;

(H) (4-(2-hydroxyethyl)-1-piperazinylacetyl)Phe-D-Cys-Tyr-D-Trp-Lys-Thr-Cys-2R-(2-naphthyl)ethylamide;

(H) (4-(2-hydroxyethyl)-1-piperizineethanesulfonyl)Phe-D-Cys-Tyr-D-Trp-Lys-Thr-Cys-2R-(2-naphthyl)ethylamide;

H$_2$-Phe-D-Cys-Pal-D-Trp-Lys-Thr-Cys-2R-(2-naphthyl)ethylamide;

(H) (CH$_3$CO)Phe-D-Cys-Pal-D-Trp-Lys-Thr-Cys-2R-(2-naphthyl)ethylamide;

(H) (4-(2-hydroxyethyl)-1-piperazinylacetyl)Phe-D-Cys-Pal-D-Trp-Lys-Thr-Cys-2R-(2-naphthyl)ethylamide;

(H) (4-(2-hydroxyethyl)-1-piperizineethanesulfonyl)Phe-D-Cys-Pal-D-Trp-Lys-Thr-Cys-2R-(2-naphthyl)ethylamide;

H$_2$-β-Nal-D-Cys-Tyr-D-Trp-Lys-Abu-Cys-2R-(2-naphthyl)ethylamide;

H$_2$-Phe-D-Cys-Tyr-D-Trp-Lys-Abu-Cys-2R-(2-naphthyl)ethylamide;

H$_2$-β-Nal-D-Cys-Tyr-D-Trp-Lys-Abu-Cys-2R,3R-(2-hydroxymethyl)-3-hydroxy)propylamide;

H$_2$-Phe-D-Cys-Tyr-D-Trp-Lys-Abu-Cys-2R,3R-(2-hydroxymethyl)-3-hydroxy)propylamide;

H$_2$-Phe-D-Phe-Tyr-D-Trp-Lys-Thr-Phe-Thr-NH$_2$;

H$_2$-Phe-D-Phe-Tyr-D-Trp-Lys-Val-Phe-Thr-NH$_2$;

H$_2$-Phe-D-Cpa-Tyr-D-Trp-Lys-Val-Phe-Thr-NH$_2$;

H$_2$-β-Nal-D-Cpa-Tyr-D-Trp-Lys-Val-Phe-Thr-NH$_2$ (Analog No. 1);

(H) (CH$_3$CO)-β-Nal-D-Cpa-Tyr-D-Trp-Lys-Val-Phe-Thr-NH$_2$;

(H) (4-(2-hydroxyethyl)-1-piperazinylacetyl)-β-Nal-D-Cpa-Tyr-D-Trp-Lys-Val-Phe-Thr-NH$_2$;

(H) (4-(2-hydroxyethyl)-1-piperizineethanesulfonyl)-β-Nal-D-Cpa-Tyr-D-Trp-Lys-Val-Phe-Thr-NH$_2$;

H$_2$-β-Nal-D-Cpa-Pal-D-Trp-Lys-Val-Phe-Thr-NH$_2$;

(H) (CH$_3$CO)-β-Nal-D-Cpa-Pal-D-Trp-Lys-Val-Phe-Thr-NH$_2$;

(H) (4-(2-hydroxyethyl)-1-piperazinylacetyl)-β-Nal-D-Cpa-Pal-D-Trp-Lys-Val-Phe-Thr-NH$_2$;

(H) (4-(2-hydroxyethyl)-1-piperizineethanesulfonyl)-β-Nal-D-Cpa-Pal-D-Trp-Lys-Val-Phe-Thr-NH$_2$;

H$_2$-β-Nal-D-Cpa-Tyr-D-Trp-Lys-Thr-Phe-Thr-NH$_2$;

(H) (CH$_3$CO)-β-Nal-D-Cpa-Tyr-D-Trp-Lys-Thr-Phe-Thr-NH$_2$;

(H) (4-(2-hydroxyethyl)-1-piperazinylacetyl)-β-Nal-D-Cpa-Tyr-D-Trp-Lys-Thr-Phe-Thr-NH$_2$;

(H) (4-(2-hydroxyethyl)-1-piperizineethanesulfonyl)-β-Nal-D-Cpa-Tyr-D-Trp-Lys-Thr-Phe-Thr-NH$_2$;

H$_2$-β-Nal-D-Cpa-Pal-D-Trp-Lys-Thr-Phe-Thr-NH$_2$;

(H) (CH$_3$CO)-β-Nal-D-Cpa-Pal-D-Trp-Lys-Thr-Phe-Thr-NH$_2$;

(H) (4-(2-hydroxyethyl)-1-piperazinylacetyl)-β-Nal-D-Cpa-Pal-D-Trp-Lys-Thr-Phe-Thr-NH$_2$;

(H) (4-(2-hydroxyethyl)-1-piperizineethanesulfonyl)-β-Nal-D-Cpa-Pal-D-Trp-Lys-Thr-Phe-Thr-NH$_2$;

H$_2$-β-Nal-D-Cpa-Tyr-D-Trp-Lys-Val-Phe-β-Nal-NH$_2$;

(H) (CH$_3$CO)-β-Nal-D-Cpa-Tyr-D-Trp-Lys-Val-Phe-β-Nal-NH$_2$;

(H) (4-(2-hydroxyethyl)-1-piperazinylacetyl)-β-Nal-D-Cpa-Tyr-D-Trp-Lys-Val-Phe-β-Nal-NH$_2$; or (H) (4-(2-hydroxyethyl)-1-piperizineethanesulfonyl)-β-Nal-D-Cpa-Tyr-D-Trp-Lys-Val-Phe-β-Nal-NH$_2$;

H$_2$-β-Nal-D-Cpa-Tyr-D-Trp-Lys-Val-Phe-β-Nal-NH$_2$ (Analog No. 23);

H$_2$-β-Nal-D-Cpa-Tyr-D-Trp-Lys-Val-Phe-Thr-NH$_2$;

H$_2$-D-β-Nal-D-Cpa-Phe-D-Trp-Lys-Val-Phe-Thr-NH$_2$;

H$_2$-D-β-Nal-D-Phe-Tyr-D-Trp-Lys-Thr-Phe-Thr-NH$_2$;

H$_2$-D-Phe-D-Phe-Tyr-D-Trp-Lys-Val-Phe-Thr-NH$_2$;

H$_2$-D-β-Nal-D-Cpa-Tyr-D-Trp-Lys-Val-Phe-Thr-NH$_2$ (Analog No. 8); or

H$_2$-D-β-Nal-D-Cpa-Tyr-D-Trp-Lys-Val-Phe-β-Nal-NH$_2$; or a pharmaceutically acceptable salt thereof.

With the exception of the N-terminal amino acid, all abbreviations (e.g., Ala or A$_2$) of amino acids in this disclosure stand for the structure of —NH—CH(R)—CO—, wherein R is a side chain of an amino acid (e.g., CH$_3$ for Ala). For the N-terminal amino acid, the abbreviation stands for the structure of =N—CH(R)—CO—, wherein R is a side chain of an amino acid. Pen, β-Ala, Gaba, Nle, Nva, Pal, F$_5$-Phe, 2,4-dichloro-Phe, Cpa, β-Nal, β-1-Nal, Abu, Dip, 2-Pal, Bip, Npa, Igl, Bta, Tle, Bpa, Iph, Cha, Thr(Bzl), Tyr(Bzl), and Aib are respective abbreviations of the following α-amino acids: penicillamine, 3-aminopropionic acid, 4-aminobutyric acid, norleucine, norvaline, β-[3-pyridyl]-alanine, β-[2,3,4,5,6-pentafluorophenyl]-alanine, β-[2,4-dichlorophenyl]-alanine, β-[4-chlorophenyl]-alanine, β-[2-napthyl]-alanine, β-[1-naphthyl]-alanine; 2-aminobutyric acid, 3,3'-diphenylalanine, β-[2-pyridyl]-alanine, 4,4'-biphenylalanine, p-NO$_2$-phenylalanine, 2-indanylglycine, 3-benzothienylalanine, α-[t-butyl]- glycine, 4-bromo-phenylalanine, 4-iodo-phenylalanine, β-(cyclohexyl)-alanine, O-benzyl-threonine, O-benzyl-tyrosine, and 2-aminoisobutyric acid. Tyr(I) refers to an iodinated tyrosine residue (e.g., 3-I-Tyr, 5-I-Tyr, 3,5-I-Tyr) wherein the iodine may be a radioactive isotope, e.g., $I^{125}$, $I^{127}$, or $I^{131}$. An aliphatic amino acid is an α-amino acid having one or two side chains which, independently, are hydrocarbons, e.g., a straight or branched chain of 1–6 carbons. Examples of aliphatic amino acids include Ala, Aib, Val, Leu, Tle, Ile, Nle, Nva, or Abu. An aromatic amino acid is an α-amino acid the side chain of which has a neutral (e.g., not acidic or basic) aromatic substituent, e.g., a substituted or unsubstituted phenyl, naphthyl, or aromatic heterocycle group (e.g., pyridyl or indolyl). Examples of aromatic amino acids include Phe, p-X-Phe (where X is a halo (e.g., F, Cl, Br, or I), OH, $OCH_3$, $CH_3$, or $NO_2$), o-X-Phe (where X is a halo, OH, $OCH_3$, $CH_3$, or $NO_2$), m-X-Phe (where X is a halo, OH, $OCH_3$, $CH_3$, or $NO_2$), His, Pal, Trp, β-Nal, 2,4-dichloro-Phe, Tyr(I), β-[3,4,5-trifluorophenyl]-alanine, Bta, β-[3-cyanophenyl]-alanine, β-[4-cyanophenyl]-alanine, β-[3,4-difluorophenyl]-alanine, β-[3,5-difluorophenyl]-alanine, β-[2-fluorophenyl]-alanine, β-[4-thiazolyl]-alanine, Bip, Dip, Npa, Igl, Bpa, Iph, homophenylalanine, 2-Pal, β-[4-pyridyl]-alanine, β-[4-thiazolyl]-alanine, β-[2-thiazolyl]-alanine, para-($CF_3$)-phenylalanine, and $F_5$-Phe. What is meant by an "Eaa" is an amino acid of the formula —NH—[CH(R)$_r$—CO— (where n is 2–6 and R is H, lower alkyl, or hydroxy lower alkyl). Examples of an Eaa include β-Ala and Gaba.

As used herein, "lower alkyl" is intended to include both branched and straight-chain saturated aliphatic hydrocarbon groups having 1–6 carbon atoms. Examples of lower alkyl groups include methyl, ethyl, propyl, isopropyl, butyl, t-butyl, isobutyl, sec-butyl, and the like.

As used herein, "aryl" is intended to include any stable monocyclic, bicyclic, or tricyclic carbon ring(s) of up to 7 members in each ring, wherein at least one ring is aromatic. Examples of aryl groups include phenyl, naphthyl, anthracenyl, biphenyl, tetrahydronaphthyl, indanyl, phenanthrenyl, and the like.

The term "heterocyclyl", as used herein, represents a stable 5- to 7-membered monocyclic or stable 8- to 11-membered bicyclic or stable 11–15 membered tricyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothio-pyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperidinyl, 2-oxopyrrolidinyl, piperidyl, piperazinyl, pyridyl, pyridyl N-oxide, quinoxalinyl, tetrahydrofuryl, tetrahydroisoquinolinyl, tetrahydro-quinolinyl, thiamorpholinyl, thiamorpholinyl sulfoxide, thiazolyl, thiazolinyl, thienofuryl, thienothienyl, thienyl, and the like.

The term "substituted" is meant to include the recited chemical group (e.g., lower alkyl, heterocycle, aryl, cycloalkyl, etc.) substituted with one to four of the recited substituents (e.g., halo, hydroxy, lower alkyl, etc.). The substituent may be attached to any atom in the chemical group.

The structure of 4-(2-hydroxyethyl)]-1-piperazinylacetyl and 4-(2-hydroxyethyl)]-1-piperizineethanesulfonyl are, respectively, as follows:

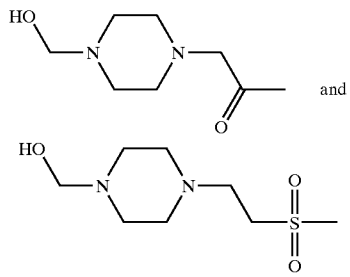

The compounds of this invention can be provided in the form of pharmaceutically acceptable salts. Acceptable salts include, but are not limited to, acid addition salts of inorganic acids such as hydrochloride, sulfate, phosphate, diphosphate, hydrobromide, and nitrate or organic acids such as acetate, maleate, fumarate, tartrate, succinate, citrate, lactate, methanesulfonate, p-toluenesulfonate, pamoate, salicylate, oxalate, and stearate. Also within the scope of the present invention, where applicable, are salts formed from bases such as sodium or potassium hydroxide. For further examples of pharmaceutically acceptable salts see, "Pharmaceutical Salts," J. Pharm. Sci. 66:1 (1977).

Where the amino acid residue is optically active, it is the L-isomer that is intended unless otherwise specified. In the formulae set forth herein, the disulfide bond between the thiol group on the side chain of residue $A_2$ (e.g., Cys, Pen, D-Cys, or D-Pen) and the thiol group on the side chain of residue $A_7$ (e.g., Cys or Pen) is not shown.

The peptides of the invention can be used to promote the release of growth hormone or insulin in a subject (e.g., a mammal such as a human patient). Thus, the peptides are useful in the treatment of physiological conditions in which the promotion of the release of growth hormone or insulin is of benefit. The peptides of the invention can also be used in enhancing wound healing or promoting angiogenesis. Also, peptides of the invention having a Tyr(I) residue can be used to image cells containing somatostatin receptors. Such peptides of the invention can be used either in vivo to detect cells having somatostatin receptors (e.g., cancer cells) or in vitro as a radioligand in a somatostatin receptor binding assay. The peptide of the invention can also be used as vectors to target cells with radioactive isotopes.

A therapeutically effective amount of a peptide of this invention and a pharmaceutically acceptable carrier substance (e.g., magnesium carbonate, lactose, or a phospholipid with which the therapeutic compound can form a micelle) together form a therapeutic composition (e.g., a pill, tablet, capsule, or liquid) for administration (e.g., orally, intravenously, transdermally, pulmonarily, vaginally, subcutaneously, nasally, iontophoretically, or by intratracheally) to a subject in need of the peptide. The pill, tablet, or capsule can be coated with a substance capable of protecting the composition from the gastric acid or intestinal enzymes in the subject's stomach for a period of time sufficient to allow the composition to pass undigested into the subject's small intestine. The therapeutic composition can also be in the form of a biodegradable or nonbiodegradable sustained release formulation for subcutaneous or intramuscular administration. See, e.g., U.S. Pat. Nos. 3,773,919 and 4,767,628 and PCT Application No. WO 94/00148. Continuous administration can also be obtained using an implantable or external pump (e.g., INFUSAID™ pump) to administer the therapeutic composition.

The dose of a peptide of the present invention for treating the above-mentioned diseases or disorders varies depending upon the manner of administration, the age and the body weight of the subject, and the condition of the subject to be treated, and ultimately will be decided by the attending physician or veterinarian. Such an amount of the peptide as determined by the attending physician or veterinarian is referred to herein as a "therapeutically effective amount."

Also contemplated within the scope of this invention is a peptide covered by the above generic formula for both use in treating diseases or disorders associated with the need to promote the release of growth hormone or insulin, and use in detecting somatostatin receptors, e.g., radioimaging.

Other features and advantages of the present invention will be apparent from the detailed description and from the claims.

DETAILED DESCRIPTION OF THE INVENTION

It is believed that one skilled in the art can, based on the description herein, utilize the present invention to its fullest extent. The following specific embodiments are, therefore, to be construed as merely illustrative, and not limitative of the remainder of the disclosure in any way whatsoever.

Unless defined otherwise, all technical and scientific terms used herein have the same meaning as commonly understood by one of ordinary skill in the art to which this invention belongs. Also, all publications, patent applications, patents, and other references mentioned herein are incorporated by reference.

Synthesis

The synthesis of short peptides is well examined in the peptide art. See e.g., Stewart, et al., Solid Phase Peptide Synthesis (Pierce Chemical Co., 2d ed., 1984). The following describes the synthesis of D-β-Nal-Cys-Pal-D-Trp-Lys-Val-Cys-β-Nal-NH$_2$ and D-β-Nal-Cpa-Tyr-D-Trp-Lys-Val-Phe-Thr-NH$_2$. Other peptides of the invention can be prepared in an analogous manner by a person of ordinary skill in the art.

(a) Synthesis of H$_2$-β-Nal-D-Cys-Pal-D-Trp-Lys-Val-Cys-β-Nal-NH$_2$

1) Boc-β-Naphthylalanine-S-methylbenzyl-D-cysteine-3-pyridyl-2-alanine-D-tryptophan-N$^e$-benzyloxycarbonyl-lysine-valine-S-methylbenzyl-cysteine-β-naphthylalanine-benzhydrylamine Resin.

Benzhhydrylamine-polystyrene resin (Advanced ChemTech, Inc., Louisville, Ky.) (1.2 g; 0.5 mmole) in the chloride ion form was placed in the reaction vessel of an Advanced ChemTech™ peptide synthesizer programmed to perform the following reaction cycle: (a) methylene chloride; (b) 33% trifluoroacetic acid in methylene chloride (2 times for 1 and 25 min each); (c) methylene chloride; (d) ethanol; (e) methylene chloride; and (f) 10% triethylamine in chloroform.

The neutralized resin was stirred with Boc-O-β-naphthylalanine and diisopropylcarbodiimide (1.5 mmole each) in methylene chloride for 1 hr, and the resulting amino acid resin was then cycled through steps (a) to (f) in the above wash program. The following amino acids (1.5 mmole) were then coupled successively by the same procedure: Boc-S-methylbenzyl-Cys, Boc-Val, Boc-Ne-benzyloxycarbonyl-lysine, Boc-D-Trp, Boc-Pal, and Boc-S-methylbenzyl-D-Cys and Boc-β-Nal. After washing and drying, the completed resin weighed 2.0 g.

2) β-Naphthylalanine-c[D-cysteine-3-pyridyl-2-alanine-D-tryptophan-lysine-valine-cysteine]-β-naphthylalanine-NH$_2$ The completed resin described in (1) (1.0 g, 0.25 mmole) was mixed with anisole (5 ml), dithiothreitol (100 mg), and anhydrous hydrogen fluoride (35 ml) at 0° C. and stirred for 45 min. Excess hydrogen fluoride was evaporated rapidly under a stream of dry nitrogen, and the free peptide is precipitated and washed with ether. The crude peptide was then dissolved in 500 ml of 90% acetic acid to which was added a concentrated solution of I$_2$/MeOH until a permanent brown color is observed. Excess I$_2$ is removed by addition of ascorbic acid and the solution evaporated to a small volume which was applied to a column (2.5×90 cm) of Sephadex™ G-25, which was eluted with 50% AcOH. Fractions containing a major component by ultraviolet (UV) absorption and thin layer chromatography were then pooled, evaporated to a small volume, and applied to a column (1.5×70 cm) of Vydac™ octadecylsilane silica (10–15 μm). This was eluted with a linear gradient of acetonitrile in 0.1% trifluoroacetic acid in water. Fractions were examined by thin layer chromatography (TLC) and analytical high performance liquid chromatography (HPLC) and pooled to give maximum purity. Repeated lyophilization of the solution from water gave the desired product as a white, fluffy powder. The product was found to be homogeneous by HPLC and TLC. Amino acid analysis of an acid hydrolysate and matrix-assisted laser desorption (MALD) mass spectroscopy confirmed the composition of the octapeptide.

(b) Synthesis of H$_2$-D-β-Nal-Cpa-Tyr-D-Trp-Lys-Val-Phe-Thr-NH$_2$

1) Boc-β-D-Naphthylalanine-D-4-chlorophenylalanine-O-dichlorobenzyl-tyrosine-D-tryptophan-N$^e$-benzyloxycarbonyl-lysine-valine-S-phenylalanine-O-benzyl-threonine-benzhydrylamine Resin Benzhydrylamine-polystyrene resin (Advanced ChemTech™, Inc.) (1.2 g, 0.5 mmole) in the chloride ion form was placed in the reaction vessel of an Advanced ChemTech peptide synthesizer programmed to perform the following reaction cycle: (a) methylene chloride; (b) 33% trifluoroacetic acid in methylene chloride (2 times for 1 and 25 min each); (c) methylene chloride; (d) ethanol; (e) methylene chloride; and (f) 10% triethylamine in chloroform.

The neutralized resin was stirred with Boc-O-benzylthreonine and diisopropylcarbodiimide (1.5 mmole each) in methylene chloride for 1 hr and the resulting amino acid resin was cycled through steps (a) to (f) in the above wash program. The following amino acids (1.5 mmole) were then coupled successively by the same procedure: Boc-phenylalanine, Boc-Val, Boc-N$^e$-benzyloxycarbonyl-lysine, Boc-D-Trp, Boc-O-dichlorobenzyl-Tyr, and Boc-D-4-chlorophenylalanine, and Boc-β-D-Nal. After washing and drying, the completed resin weighed 2.1 g.

2) β-D-Naphthylalanine-D-4-chlorophenylalanine-tyrosine-D-tryptophan-lysine-valine-phenylalanine-threonine-NH$_2$ The peptide resin from (1) was subjected to HF cleavage as described above. Column purification as described yielded the desired compound as a white, fluffy powder (170 mg) which is found to be homogeneous by HPLC and TLC. Amino acid analysis of an acid hydrolysate and MALD mass spectroscopy confirms the composition of the peptide.

Peptides containing C-terminal substituted amides can be made by solid phase methods by displacing the appropriate peptide off the solid phase with the corresponding amine. Alternatively, these analogs may be synthesized by solution-phase peptide synthesis methods in which the growing peptide chain is maintained in solution in an organic solvent during synthesis and assembled by iterative coupling/deprotection cycles. Final removal of the side chain protecting groups yields the desired peptide after appropriate purification. Peptides containing N-terminal substitutions (e.g., where $R_1$ is E, CO, or $E_1SO_2$ (where $E_1$ is heterocycle lower alkyl) substituted with hydroxy lower alkyl and $R_2$ is H such as 4-(2-hydroxyethyl)-1-piperazinylacetyl or 4-(2-hydroxyethyl)-1-piperdineethanesulfonyl) can be synthesized as described in PCT Application No. WO 95/04752.

Bioassay on the In Vitro Release of Growth Hormone (a) Rat Pituitary Cell Dispersion Pituitaries from adult Charles River CD male rats (Wilmington, Mass.) housed under controlled conditions were dispersed and cultured using aseptic technique by modification of previously described methods (Hoefer, M. T., et al., Mol. Cell. Endocrinol. 35:229 (1984); Ben-Jonathan, N., et al., Methods Enzymol. 103:249 (1983); and Heiman, M. L., et al., Endocrinology 116:410 (1985)). Pituitaries were removed from sacrificed rats, sectioned, and then placed into a siliconized, liquid scintillation vial containing 2 ml 0.2% trypsin (Worthington Biochemicals, Freehold, N.J.) in sterile-filtered Krebs-Ringer bicarbonate buffer supplemented with 1% bovine serum albumin, 14 mM glucose, modified Eagle medium (MEM) vitamin solution, and MEM amino acids (Gibco Laboratories, Grand Island, N.Y.) (KRBGA). All glassware was siliconized as described by Sayers, et al., Endocrinology 88:1063 (1971). The fragments were incubated in a water bath for 35 min at 37° C. with agitation. The vial contents then were poured into a scintillation vial containing 2 ml 0.1% DNase (Sigma Chemical Co., St. Louis, Mo.) in KRBGA and incubated for 2 min at 37° C. with agitation. After incubation, the tissue was decanted into a 15 ml centrifuge tube and allowed to settle. Medium was discarded, and pituitary sections were washed 3 times with 1 ml fresh KRBGA. The cells were then dispersed in 2 ml 0.05% LBI (lima bean trypsin inhibitor, Worthington Biochemicals) by gently drawing the fragments into and expelling them out of a siliconized, fire polished Pasteur pipette. Dispersed cells were then filtered through a 630 μm diameter Nylon mesh (Tetko, Elmsford, N.Y.) into a fresh 15 ml centrifuge tube. An additional 2 ml of 0.05% LBI solution was used to rinse the first tube and was transferred to the second tube with filtering.

(b) Cell Culture

The dispersed cells were then further diluted with approximately 15 ml sterile-filtered Dulbecco's modified Eagle medium (GIBCO), which was supplemented with 2.5% fetal calf serum (GIBCO), 3% horse serum (GIBCO), 10% fresh rat serum (stored on ice for no longer than 1 hr) from the pituitary donors, 1% MEM non-essential amino acids (GIBCO), and gentamycin (10 ng/ml; Sigma) and nystatin (10,000 U/ml; GIBCO). The cells were poured into a 50 ml round-bottomed glass extraction flask with a large diameter opening and then randomly plated at a density of approximately 200,000 cells per well (Co-star cluster 24; Rochester Scientific Co., Rochester, N.Y.). The plated cells were maintained in the above Dulbecco's medium in a humidified atmosphere of 95k air and 5% $CO_2$ at 37° C. for 4–5 days.

(c) Experimental Incubation and $IC_{50}$ Determination

In preparation for a hormone challenge, the cells were washed 3 times with medium 199 (GIBCO) to remove old medium and floating cells. Each treatment well contained a total volume of 1 ml medium 199 containing 1% BSA (fraction V; Sigma) with treatments as described below. Each antagonist candidate was tested using a single 24-well cell culture plate. Each treatment was performed in triplicate. Each plate contained 8 treatment groups: one 1 nM growth hormone releasing factor (GRF) (1–29)$NH_2$-stimulated control group; one 1 nM somatostatin-inhibited control group in the presence of 1 nM GRF(1–29)$NH_2$; and 6 doses of a given antagonist in the presence of both 1 nM SRIF and 1 nM GRF per plate. After 3 hrs at 37° C. in a air/carbon dioxide atmosphere (95/5%), the medium was removed and stored at −20° C. until radioimmunoassayed for growth hormone content. $IC_{50}$'s of each antagonist versus 1 nM SRIF were calculated using a computer program (SigmaPlot, Jandel Scientific, San Rafael, Calif.) with the maximum response constrained to the value of the 1 nM GRF(1–29)$NH_2$-stimulated control. These $IC_{50}$'s are presented in Table I.

TABLE I

| ANALOG No. | $IC_{50}$ (μM) |
|---|---|
| 1 | 3.03 |
| 2 | 0.04 |
| 3 | 0.01 |
| 4 | 0.03 |
| 5 | 0.06 |
| 6 | 0.9 |
| 7 | 0.071 |
| 8 | 3.96 |
| 9 | 1.36 |
| 10 | 0.62 |
| 11 | 0.72 |
| 12 | 0.056 |
| 13 | 0.11 |
| 14 | 0.11 |
| 15 | 0.14 |
| 16 | 0.82 |
| 17 | 1 |
| 18 | 0.38 |
| 19 | 0.11 |
| 20 | 0.12 |
| 21 | 0.97 |
| 22 | 0.066 |
| 23 | 0.91 |
| 24 | 0.068 |
| 25 | 0.28 |
| 26 | 0.38 |
| 27 | 0.041 |
| 28 | 0.10 |
| 29 | 0.0084 |
| 30 | 0.0065 |
| 31 | 0.0038 |
| 32 | 0.012 |
| 33 | 1.50 |
| 34 | 0.42 |
| 35 | 0.052 |
| 36 | 1.03 |
| 37 | 0.78 |
| 38 | 0.11 |
| 39 | 0.034 |
| 40 | 0.11 |
| 41 | 0.21 |
| 42 | 0.044 |
| 43 | 0.00082 |
| 44 | 0.021 |
| 45 | 0.13 |
| 46 | 0.02 |
| 47 | 0.053 |
| 48 | 0.050 |
| 49 | 0.23 |

TABLE I-continued

| ANALOG No. | IC$_{50}$ ($\mu$M) |
|---|---|
| 50 | 0.0011 |
| 51 | 0.012 |
| 52 | 0.0026 |
| 53 | 0.0029 |
| 54 | 0.029 |
| 55 | 0.0026 |
| 56 | 0.0018 |
| 57 | 0.0059 |

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A compound of the formula:

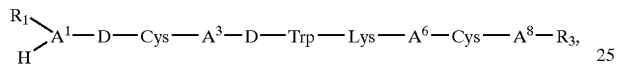

or a pharmaceutically acceptable salt thereof, wherein
$A^1$ is deleted;
$A^3$ is an aromatic amino acid;
$A^6$ is Thr, Thr(Bzl), Gly, Ser, an Eaa or an aliphatic amino acid;
$A^8$ is a D- or L-isomer selected from the group consisting of Thr, Ser, an aromatic amino acid and an aliphatic amino acid;
$R_1$ is substituted or unsubstituted $E_1CO$ wherein $E_1$ is aryl, aryl lower alkyl, heterocycle or heterocycle lower alkyl; and
$R_3$ is OH, $NH_2$, $C_{1-12}$ alkoxy or NH—Y—$CH_2$—Z, wherein Y is a $C_{1-12}$ hydrocarbon moiety and Z is H, OH, $CO_2H$ or $CONH_2$; or $R_3$, together with the carbonyl group of $A^8$ attached thereto, are reduced to form H, lower alkyl or hydroxy lower alkyl;
provided that a disulfide bond links the sidechains of $A^2$ and $A^7$.

2. A compound of claim 1, wherein $R_1$ is substituted or unsubstituted $E_1CO$ and $E_1$ is phenyl, β-naphthylmethyl, β-pyridinylmethyl, or 3-indolylmethyl; $A^3$ is β-Nal, o-X-Phe wherein X is H, OH, $CH_3$, halo, $OCH_3$, $NH_2$, CN, or $NO_2$, p-X-Phe wherein X is H, OH, $CH_3$, halo, $OCH_3$, $NH_2$, CN, or $NO_2$, m-X-Phe wherein X is H, OH, $CH_3$, halo, $OCH_3$, $NH_2$, CN, or $NO_2$, $F_5$-Phe, Trp, Dip, 2-Pal, Tyr(Bzl), His, Igl, Tyr(I), Bta, Bip, Npa, or Pal; $A^6$ is Thr, Ser, Tle, Thr(Bzl), Abu, Ala, Ile, Leu, Gly, Nle, β-Ala, Gaba, or Val; and $A^8$ is the D- or L-isomer of Thr, Dip, $F_5$-Phe, p-X-Phe wherein X is H, OH, $CH_3$, halo, $OCH_3$, $NH_2$, CN, or $NO_2$, o-X-Phe wherein X is H, OH, $CH_3$, halo, $OCH_3$, $NH_2$, CN, or $NO_2$, m-X-Phe wherein X is H, OH, $CH_3$, halo, $OCH_3$, $NH_2$, CN, or $NO_2$, Igl, Tyr(Bzl), or β-Nal.

3. A compound of claim 2, wherein $R_1$ is $E_1CO$ and $E_1$ is 4-hydroxy-phenyl, β-naphthylmethyl, or phenyl; $A^3$ is Tyr, Tyr(I), or Pal; $A^6$ is Val, Tle, Nle, Ile, or Leu; $A^8$ is p-F-Phe, β-Nal, Tyr, Dip, p-Cl-Phe, Igl, or p-CN-Phe; and $R_3$ is $NH_2$.

4. A compound of claim 3, wherein $A^3$ is Pal.

5. A compound of claim 2, of the formula
(H) (3-phenylpropionyl)-D-Cys-Tyr-D-Trp-Lys-Val-Cys-β-Nal-$NH_2$;
(H) (3-phenylpropionyl)-D-Cys-Pal-D-Trp-Lys-Val-Cys-β-Nal-$NH_2$;
(H) (3-phenylpropionyl)-D-Cys-Tyr-D-Trp-Lys-Thr-Cys-β-Nal-$NH_2$;
(H) (3-phenylpropionyl)-D-Cys-Pal-D-Trp-Lys-Thr-Cys-β-Nal-$NH_2$;
(H) (3-phenylpropionyl)-D-Cys-Tyr-D-Trp-Lys-Val-Cys-Thr-$NH_2$;
(H) (3-phenylpropionyl)-D-Cys-Pal-D-Trp-Lys-Val-Cys-Thr-$NH_2$;
(H) (3-phenylpropionyl)-D-Cys-Tyr-D-Trp-Lys-Thr-Cys-Thr-$NH_2$;
(H) (3-phenylpropionyl)-D-Cys-Pal-D-Trp-Lys-Thr-Cys-Thr-$NH_2$;
(H) (3-[2-naphthyl]propionyl)-D-Cys-Tyr-D-Trp-Lys-Val-Cys-β-Nal-$NH_2$;
(H) (3-[2-naphthyl]propionyl)-D-Cys-Tyr-D-Trp-Lys-Val-Cys-β-Nal-$NH_2$;
(H) (3-[2-naphthyl]propionyl)-D-Cys-Pal-D-Trp-Lys-Val-Cys-β-Nal-$NH_2$;
(H) (3-[2-naphthyl]propionyl)-D-Cys-Tyr-D-Trp-Lys-Thr-Cys-β-Nal-$NH_2$;
(H) (3-[2-naphthyl]propionyl)-D-Cys-Pal-D-Trp-Lys-Thr-Cys-β-Nal-$NH_2$;
(H) (3-[2-naphthyl]propionyl)-D-Cys-Tyr-D-Trp-Lys-Val-Cys-Thr-$NH_2$;
(H) (3-[2-naphthyl]propionyl)-D-Cys-Pal-D-Trp-Lys-Val-Cys-Thr-$NH_2$;
(H) (3-[2-naphthyl]propionyl)-D-Cys-Tyr-D-Trp-Lys-Thr-Cys Thr-$NH_2$;
(H) (3-[2-naphthyl]propionyl)-D-Cys-Pal-D-Trp-Lys-Thr-Cys Thr-$NH_2$;
(H) (3-[p-hydroxyphenyl])-D-Cys-Tyr-D-Trp-Lys-Val-Cys-β-Nal-$NH_2$;
(H) (3-naphthyl]propionyl)-D-Cys-Tyr-D-Trp-Lys-Abu-Cys-β-Nal-$NH_2$;
(H) (3-naphthyl]propionyl)-D-Cys-Tyr-D-Trp-Lys-Abu-Cys-Thr-$NH_2$;
(H) (3-phenylylpropionyl)-D-Cys-Tyr-D-Trp-Lys-Abu-Cys-β-Nal-$NH_2$; or
(H) (3-phenylylpropionyl)-D-Cys-Tyr-D-Trp-Lys-Abu-Cys-Thr-$NH_2$; or
a pharmaceutically acceptable salt thereof.

* * * * *